United States Patent [19]

Batorewicz

[11] Patent Number: 4,723,040
[45] Date of Patent: Feb. 2, 1988

[54] PROCESS FOR MAKING N-MONO-SUBSTITUTED P-PHENYLENEDIAMINES

[75] Inventor: Wadim Batorewicz, New Haven, Conn.

[73] Assignee: Uniroyal Chemical Company, Inc., Middlebury, Conn.

[21] Appl. No.: 944,262

[22] Filed: Dec. 19, 1986

Related U.S. Application Data

[63] Continuation of Ser. No. 753,742, Jun. 10, 1985.

[51] Int. Cl.$^4$ ............................................. C07C 85/11
[52] U.S. Cl. .................................. 564/416; 564/410; 564/411; 564/419
[58] Field of Search ................ 564/410, 411, 416, 419

[56] References Cited

U.S. PATENT DOCUMENTS

| | | | |
|---|---|---|---|
| 1,948,330 | 2/1934 | Calvert | 564/416 |
| 2,163,617 | 6/1939 | Mow | 564/416 |
| 3,248,427 | 4/1966 | Greenfield | 564/416 |
| 3,253,038 | 5/1966 | Wise | 564/416 |
| 4,448,994 | 5/1984 | Kurek | 564/416 |
| 4,518,803 | 5/1985 | Bartovewicz et al. | 564/410 |

Primary Examiner—Charles F. Warren
Assistant Examiner—John A. Sopp
Attorney, Agent, or Firm—John A. Shedden

[57] ABSTRACT

A process for preparing an N-mono-substituted-p-phenylenediamine by reacting the corresponding p-nitroso-N-mono-substituted aniline compound with a primary or secondary alcohol in the presence of a base.

6 Claims, No Drawings

PROCESS FOR MAKING N-MONO-SUBSTITUTED P-PHENYLENEDIAMINES

This is a continuation of application Ser. No. 753,742, filed June 10, 1985.

BACKGROUND OF THE INVENTION

It has long been desired to develop an efficient and economical process for the manufacture of N-monosubstituted p-phenylenediamines. These materials are particularly useful for the manufacture of antioxidants and antiozonants for use in rubber products and as intermediates for the preparation of dyes.

Conventionally, these materials have been prepared by the hydrogenation of nitrosoarylamines as a salt of an alkali metal in an aqueous system. Reduction is typically performed using gaseous hydrogen in the presence of a conventional hydrogenation catalyst. An example of this process is shown in U.S. Pat. No. 2,974,169.

In later work, such as described in U.S. Pat. No. 4,313,002, the alkaline metal salts are reduced in other solvent systems such as aromatic hydrocarbons and saturated aliphatic alcohols. Still the hydrogenation step is taught to be performed using hydrogen over a conventional hydrogenation catalyst.

These processes suffer from the disadvantage of utilizing hydrogenation catalysts which are typically very costly noble metal catalysts such as, for example, platinum and palladium.

U.S. Pat. No. 4,448,994 teaches the use of a reducing sugar to reduce an alkaline metal salt of a nitrosoamine in an aqueous solution. This process suffers from the typical problems associated with aqueous solutions of these salts in that they tend to hydrolyze and, therefore, are unstable upon storage.

In U.S. Pat. No. 4,479,008, it is disclosed that a diphenylamine can be N-nitrosated; rearranged to form 4-nitrosodiphenylamine and subsequently hydrogenated over a conventional 5% palladium on carbon catalyst with a hydrogen pressure of 500 –800 psi at 80° C. by using an aliphatic alcohol as a medium for all of the foregoing steps. This disclosure teaches the necessity of utilizing the noble metal catalysts of the prior art for the reduction step which, as noted above, are extremely expensive.

SUMMARY OF THE INVENTION

In accordance with the invention, it has been discovered that N-mono-substituted p-phenylenediamines can be prepared by reacting 4-nitrosoanilines with alcohol under basic conditions in the absence of hydrogen and expensive noble metal catalyst. The reaction can be performed in an alcoholic solution of the same alcohol which is used as the reducing agent. In fact, all of the conventional steps usually associated with the production of 4-mono-substituted p-phenylenediamines from N-monosubstituted anilines, i.e., the N-nitrosation followed by the rearrangement to the 4-nitroso intermediate can be performed using the same alcohol which in this invention can function as the reducing agent. This process results in good yields of the desired end products with little azo and azoxy by-product formation. In addition, the N-mono-substituted p-phenylenediamine is readily separated at high levels of purity.

It is most surprising that the process of the invention would operate to produce the N-mono-substituted p-phenylenediamine. Work previously performed on nitrosobenzenes and alcohol taught that the reduction, in the presence of a base, resulted in almost quantitative yields of azoxybenzene, rather than the corresponding aminobenzene. For example, Hutton et al in "The Mechanism of Reduction of Nitrosobenzene by Alcohol", J. P. Chem. Soc. (B) 1968, pages 191–195 report this reaction. The mechanism is described on page 191 and exemplified on page 195. Interestingly, even in the heretofore mentioned patent, where the alkali metal salts of nitrosodiphenylamine were in the presence of alcohol (U.S. Pat. No. 4,313,002) it was deemed essential to effect the reduction by means of hydrogen and the conventional noble metal catalysts.

DETAILED DESCRIPTION OF THE INVENTION

The process of the invention may be described schematically as follows:

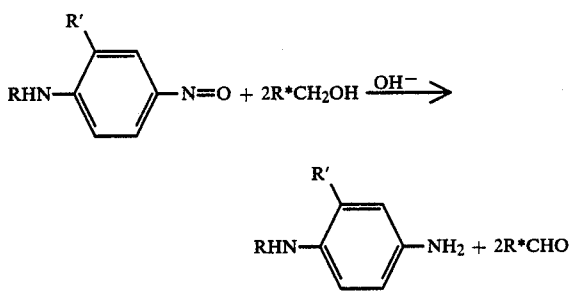

wherein R is a $C_1$–$C_{12}$ alkyl, phenyl, naphthyl, or phenyl substituted in the 2-, 4- or 2,4- positions by $C_1$–$C_8$ alkyl; R' is hydrogen or a $C_1$–$C_6$ alkyl: and R* is hydrogen, $C_1$–$C_{12}$ alkyl or phenyl.

Preferably, in the process of this invention, the alcohol has the formula R"OH wherein R" is $C_1$–$C_{12}$ alkyl or benzyl.

More preferably, the R in the above-described process is $C_3$–$C_8$ alkyl or phenyl, and R' is hydrogen or $C_1$–$C_4$ alkyl.

Most preferably, R" is $C_4$–$C_6$ alkyl.

Of the aforesaid N-mono-substituted p-phenylenediamine, the most important product is p-aminodiphenylamine. This material is useful for the preparation of well-known antioxidants; the N-alkyl-N-phenyl p-phenylenediamines. However, the process may also be readily applied to the preparation of N-isopropyl p-phenylenediamine; N-1-methylethyl p-phenylenediamine; N-cyclohexyl p-phenylenediamine; N-1,3-dimethylbutyl p-phenylenediamine; and N-1,4-dimethylpentyl p-phenylenediamine.

The alcohols which may act as a reducing agent in accordance with the teaching of the invention include the primary and secondary saturated alcohols having up to twelve carbon atoms. Examples include butanols, pentanols, hexanols, heptanols, octanols, nonanols, decanols and benzyl alcohol. Tertiary alcohols cannot be used since the presence of the alpha-hydrogen is necessary for the alcohol to act as a reducing agent.

Those skilled in the art will understand that the corresponding p-nitrosodiphenylamine may be readily selected to form the desired end product. While 4-nitrosodiphenylamine is the preferred starting material, depending on the desired end product, the following amines may also be used: 2,2'-diisopropyl, 2,2'-diisobutyl, 2,2'-di-n-butyl, 2,4'-diisopropyl; 2-isopropyl-4'- isobutyl, 4'-isopropyl, 4'-n-propyl, 4'-isobutyl, 4'-n-butyl, 4'-n-pentyl, 4'-isopentyl, 4'-n-hexyl, 4'-(2-ethylhexyl), 2,2'-diisopropyl-4'-n-butyl and 2,2'-diisobutyl-4'-n-hexyl.

The 4-nitroso-N-mono-substituted aniline can be obtained by the rearrangement of the N-nitroso derivative by contact with a mineral acid such as a hydrogen halide. This rearrangement is well known to those skilled in the art and clearly described in U.S. Pat. No. 4,313,002 and U.S. Pat. No. 4,479,008. It will be understood, that after the rearrangement it is not necessary to isolate the intermediate products.

Although other basic materials may be employed, generally, the reaction is performed in the presence of an alkali metal hydroxide.

Most preferably, the alkali metal is sodium or potassium. Sufficient base should be added to cause the reaction to go to completion and to suppress formation of azo and azoxy by-products. Generally, the base (OH)/nitroso compound (NO) molar ratio should be at least 0.75:1, preferably from 1:1 to 2:1 and most desirably from 1.25:1 to 1.5:1.

The molar ratio of the alcohol to the nitroso compound (ROH/NO) may be from 2:1 to 100:1, preferably 5:1 to 50:1 and most desirably 7.5:1 to 20:1. Enough alcohol should be present not only to reduce the nitroso compound, but also to serve as the solvent for the reaction. Generally speaking, from 20 to 30 weight percent of the nitroso compound in the alcohol is a practical concentration.

Alcohols having three or more carbon atoms are preferable to methanol and ethanol. In addition, it is desirable to minimize the water present in the process to avoid hydrolysis of the alkali metal salt. This can be done by the addition of the base in the form of a solid, rather than in the form of an aqueous solution. However, for convenience, the base may be added to the alcoholic medium in a water solution, preferably at a 50% by weight concentration.

The reaction temperature may range broadly from 50° to 200° C., but is preferably maintained between 100° and 150° C. Generally speaking, it is most convenient to carry out the reaction at atmospheric pressure, however, for lower boiling alcohols, it may be desirable to operate under higher pressures.

It is not fully understood exactly why the nitroso compounds of the instant invention behave differently than the nitrosobenzenes discussed in the Hutton et al article. However, as will be observed from the following experiments, the results are unexpectedly different. It is believed that during the reaction the alcohol is oxidized to be corresponding aldehyde or ketone, but such reaction mechanisms are of little importance in realizing the advantages of the instant invention.

To illustrate further, the invention, the following examples are set forth. In all instances, the reaction mixtures were evaluated by infrared analysis and high pressure liquid chromatography (HPLC) for the presence of the nitroso starting material and azo or azoxy byproducts, such as 4,4'-bis (N-monosubstituted amino) azoxy- and azo-benzenes. In all cases, only about 1 to 2% of each, i.e., azo and azoxy by-products, were detected.

EXAMPLE 1

Preparation of N-phenyl-p-phenylenediamine

To a 1-liter three-necked round bottom flask fitted with a stirrer, a condenser and a thermometer were added 99.0 (0.5 mole) N-phenyl-4-nitrosoaniline, 254 g n-hexanol and 40 g (0.5 mole) aqueous NaOH (50% by weight). The dark reddish brown solution was stirred, heated to 100° C., at which point an exotherm developed, and heating was discontinued. A temperature rise to 120° C. was observed within 15 minutes. After another 15 minutes, the temperature returned to 100° C. Stirring was continued for one hour while maintaining the reaction mixture at 100°–105° C. Thereafter, a sample of the reaction mixture was analyzed by HPLC; no nitroso starting material was detected.

After cooling to room temperature, the reaction mixture was washed thoroughly with water, the excess alcohol distilled off at a temperature of 165°–170° C. and at a pressure of 13.3–66.7 Pa, and the product was isolated by vacuum distillation. 77.1 g of light tancolored oily product was obtained (83.8% yield), which crystallized upon cooling. Gas chromatography indicated a product purity of 98%.

Additional experiments, reported in Table 1 below, were performed following essentially the above procedure, except for the variations noted:

TABLE I

| | RUN NO. | | | | | | | | | |
|---|---|---|---|---|---|---|---|---|---|---|
| | 1 | 2 | 3 | 4 | 5 | 6 | 7 | 8 | 9 | 10 |
| Alcohol | MEOH | MEOH | IPOH | IPOH | IBOH | MBOH | TPOH | MPOH | CHOH | ETGL |
| Reaction Temperature °C. | ca.65* | 115–125 | ca.82* | 115–125 | ca.107* | 115* | ca.102* | 100–105 | 100–105 | 100–105 |
| Reaction Period, hrs. | 1.5 | 5.7 | 2.0 | 2.0 | 3.0 | 1.5 | 5.0 | 1.0 | 1.5 | 3.0 |
| RESULTS | | | | | | | | | | |
| NPA[1] Remaining % | 100 | 50 | 100 | 0 | 0 | 0 | 100 | 0 | 0 | 16 |
| NPPD[2] Product % | — | 50 | — | 76 | 89 | 88 | — | 66 | 80 | 79 |

*Conducted at reflux temperature.
MEOH = methanol
IPOH = 2-propanol
TPOH = tertiary pentanol
IBOH = isobutyl alcohol
MBOH = 3-methyl-1-butanol
MPOH = 4-methylpentan-2-ol
CHOH = cyclohhexyl alcohol
ETGL = ethylene glycol
[1]N—phenyl-4-nitrosoaniline
[2]N—phenyl-p-phenylenediamine

EXAMPLE 2

Preparation of N-isopropyl-p-phenylenediamine

Following essentially the procedure of Example 1, 66.0 g (0.25 mole) N-isopropyl-4-nitrosoaniline, 20 g (50%) sodium hydroxide and 264 g n-hexanol were kept at 100° C. for 1.5 hours. HPLC analysis of the reaction mixture indicated absence of the nitroso starting compound. By vacuum distillation (95°–101° C. at 13.3–26.6 Pa), 31.3 g of product were recovered (48.6 wt. % yield).

EXAMPLE 3

Preparation of N-cyclohexyl-p-phenylenediamine 51.0 g (0.25 mole) N-cyclohexyl-4-nitrosoaniline, 20.0 g (50%) NaOH and 135 g n-hexanol were charged to a 0.5 liter three-necked round bottom flask equipped with stirrer, condenser and thermometer, and heated while stirring to 95° C. until the development of an exotherm was observed. Heating was discontinued, the reaction temperature continued to rise to 115° C. and then dropped, within 10 minutes, to 100° C. With the application of heat, a temperature of 90°–95° C. was maintained for 30 minutes. The reaction mixture contained no unreacted nitroso compound. The yield of the product was 64 wt. %; m.p. 59°–61° C.

EXAMPLE 4

Preparation of 2,2'Diisopropyl-N-phenyl-p-phenylenediamine 2,2'-diisopropyl-N-phenyl-4-nitrosoaniline (40.0 g, 0.167 mole), sodium hydroxide (50%; 14.0 g, 0.17 mole) and n-hexanol (120 g) were added to a reactor as described in Example 3 and, with agitation, heated to 100°–105° C. for one hour. Infrared and HPCL analyses of the reaction mixture indicated incomplete conversion. The reaction mixture was heated at 125° C. for 3.5 hours, cooled and washed several times with water. Quantitative gas chromatographic analysis of the hexanol solution indicated 73 wt. % yield.

The above embodiments and examples illustrate the scope and spirit of the instant invention. These embodiments and examples will make apparent, to those skilled in the art, other embodiments and examples. These other embodiments and examples are within the contemplation of this invention. Therefore, the instant invention should be limited only by the appended claims.

What is claimed is:

1. A process for preparing an N-mono-substituted-p-phenylenediamine which consists essentially of reacting a compound having the formula:

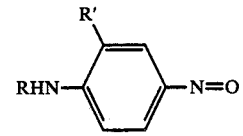

wherein R is $C_1$–$C_{12}$ alkyl, phenyl, naphthyl,, or phenyl substituted in the 2-, 4-, or 2,4- positions by $C_1$–$C_8$ alkyl; and R' is hydrogen or $C_1$–$C_6$ alkyl with a primary or secondary alcohol in the presence of a base.

2. The process of claim 1 wherein said alcohol has the formula R"OH wherein R" is $C_1$–$C_{12}$ alkyl or benzyl, and said base is an alkali metal hydroxide.

3. The process of claim 1 wherein the reaction is carried out at a temperature of from 50° to 200° C.

4. The process of claim 1 wherein R is $C_3$–$C_8$ alkyl or phenyl, and R' is hydrogen or $C_1$–$C_4$ alkyl.

5. The process of claim 2 wherein R" is $C_4$–$C_6$ alkyl, and said base is NaOH or KOH.

6. The process of claim 3 wherein the reaction temperature is from 100° to 150° C.

* * * * *